United States Patent
Misner et al.

(10) Patent No.: US 11,058,904 B2
(45) Date of Patent: Jul. 13, 2021

(54) ANTIPERSPIRANT/DEODORANT COMPOSITION

(75) Inventors: H. Steven Misner, Verona, NJ (US); Aixing Fan, Bridgewater, NJ (US); LaTonya Kilpatrick-Liverman, Princeton, NJ (US); Elizabeth Linn, Lyndhurst, NJ (US); Darrick Carlone, Morristown, NJ (US); Melissa Muir, Stewartsville, NJ (US); John P. Hogan, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 1418 days.

(21) Appl. No.: 12/671,715

(22) PCT Filed: Sep. 30, 2009

(86) PCT No.: PCT/US2009/059003
§ 371 (c)(1),
(2), (4) Date: Feb. 2, 2010

(87) PCT Pub. No.: WO2011/040911
PCT Pub. Date: Apr. 7, 2011

(65) Prior Publication Data
US 2011/0076309 A1 Mar. 31, 2011

(51) Int. Cl.
*A61Q 15/00* (2006.01)
*A61K 8/02* (2006.01)
*A61K 8/34* (2006.01)
*A61K 8/36* (2006.01)
*A61K 8/92* (2006.01)

(52) U.S. Cl.
CPC ............ *A61Q 15/00* (2013.01); *A61K 8/0229* (2013.01); *A61K 8/342* (2013.01); *A61K 8/361* (2013.01); *A61K 8/922* (2013.01)

(58) Field of Classification Search
CPC ........ A61Q 15/00; A61K 8/361; A61K 8/922; A61K 8/0229; A61K 8/342
See application file for complete search history.

(56) References Cited

U.S. PATENT DOCUMENTS

| | | |
|---|---|---|
| 2,087,162 A | 7/1937 | Moore |
| 4,265,878 A * | 5/1981 | Keil .............................. 424/68 |
| 4,280,994 A | 7/1981 | Turney |
| 4,526,780 A | 7/1985 | Marschner et al. |
| 4,724,139 A | 2/1988 | Palinczar |
| 4,822,603 A | 4/1989 | Farris et al. |
| 4,863,721 A | 9/1989 | Beck |
| 4,919,934 A | 4/1990 | Deckner |
| 4,937,069 A | 6/1990 | Shin |
| 4,944,937 A | 7/1990 | McCall |
| 5,069,897 A | 12/1991 | Orr |
| 5,102,656 A | 4/1992 | Kasat |
| 5,169,626 A | 12/1992 | Tanner et al. |
| 5,250,291 A | 10/1993 | Park |
| 5,292,530 A | 3/1994 | McCrea |
| 5,302,381 A | 4/1994 | Greczyn et al. |
| 5,429,816 A | 7/1995 | Hofrichter et al. |
| 5,508,028 A | 4/1996 | Berschied |
| 5,531,986 A | 7/1996 | Shevade et al. |
| 5,552,136 A | 9/1996 | Motley |
| 5,733,534 A | 3/1998 | Sawin |
| 5,846,520 A | 12/1998 | Guskey et al. |
| 5,916,546 A | 6/1999 | Sawin et al. |
| 5,932,275 A * | 8/1999 | Nalur ............................ 426/607 |
| 5,939,056 A | 8/1999 | Fletcher et al. |
| 6,001,341 A | 12/1999 | Calogero et al. |
| 6,007,799 A | 12/1999 | Lee et al. |
| 6,086,887 A | 7/2000 | Parrott |
| 6,096,298 A | 8/2000 | Swaile |
| 6,171,581 B1 | 1/2001 | Joshi et al. |
| 6,174,521 B1 | 1/2001 | Li et al. |
| 6,231,842 B1 * | 5/2001 | Scavone et al. ................. 424/65 |
| 6,245,366 B1 * | 6/2001 | Popplewell et al. ............ 426/96 |
| 6,277,182 B1 | 8/2001 | Lebok et al. |
| 6,352,688 B1 * | 3/2002 | Scavone et al. ................. 424/65 |

(Continued)

FOREIGN PATENT DOCUMENTS

| | | | |
|---|---|---|---|
| DE | 4009347 | 9/1991 | |
| DE | 10361526 A1 * | 7/2005 | ............... A61K 8/31 |

(Continued)

OTHER PUBLICATIONS

Gandolfo, Francois G. et al,, "Structuring of Edible Oils by Long-Chain FA, Fatty Alcohols, and Their Mixtures," JAOCS (2004) pp. 1-6, 81:1.
International Search report for PCT/US09/058957 filed Sep. 30, 2009 dated Nov. 11, 2010.
Anonymous, Herbal Stick Recipe (May 1, 2008) XP002603342 Retrieved from the internet: URL:http//web.archive.org/web/20085010061956/http://www.electronherbalism.com/Naturopathy/Recipe_and_Formulas/Stick_Deodorant_recipe.htm[retrived on Oct. 4, 2010].
Anonymous, "Vegetable fats and oils" Wikipedia XP002603382 Retrieved from the internet: URL:http://en.wikipedia.org/wiki/vegetable_fats_oils [retrieved on Oct. 5, 2010].

(Continued)

*Primary Examiner* — Robert A Wax
*Assistant Examiner* — Olga V. Tcherkasskaya

(57) ABSTRACT

A composition in which the volatile silicone is partially or fully replaced by a plant oil. The plant oil containing composition is parity or better than the volatile silicone containing material but at lower cost. One example comprises a mixing product of at least one material chosen from antiperspirant actives and deodorant actives; greater than 10 weight % of a plant oil: and less than 40 weight % of a volatile silicone oil. Another examples comprises a mixing product of greater than 10 weight % of a plant oil; a gellant for the composition; and less than 40 weight % of a volatile silicone oil, wherein the composition does not contain an antiperspirant active or deodorant active.

16 Claims, No Drawings

(56) References Cited

U.S. PATENT DOCUMENTS

| | | |
|---|---|---|
| 6,375,937 B1 | 4/2002 | Chopra et al. |
| 6,387,357 B1 | 5/2002 | Chopra et al. |
| 6,403,069 B1 | 6/2002 | Chopra et al. |
| 6,436,382 B1 | 8/2002 | Chopra et al. |
| 6,458,345 B1 | 10/2002 | Emslie |
| 6,495,097 B1 | 12/2002 | Streit |
| 6,503,491 B2 | 1/2003 | Guenin et al. |
| 6,503,944 B1 * | 1/2003 | Chanchani .................... 514/506 |
| 6,528,071 B2 * | 3/2003 | Vatter et al. .................. 424/401 |
| 6,610,648 B2 | 8/2003 | McGee et al. |
| 6,682,749 B1 * | 1/2004 | Potechin et al. .............. 424/401 |
| 6,689,932 B2 * | 2/2004 | Kruchoski et al. ........... 604/360 |
| 6,713,051 B2 | 3/2004 | Mayes et al. |
| 6,719,966 B2 | 4/2004 | Abrutyn |
| 6,805,855 B2 | 10/2004 | Mattai et al. |
| 6,849,251 B2 * | 2/2005 | Banowski et al. .............. 424/65 |
| 6,960,338 B2 | 11/2005 | Li et al. |
| 6,986,885 B2 | 1/2006 | Mattai et al. |
| 7,011,822 B2 | 3/2006 | Guenin et al. |
| 7,074,394 B2 | 7/2006 | Li et al. |
| 7,105,691 B2 * | 9/2006 | Holerca .................. C07F 7/003 556/27 |
| 7,238,343 B2 | 7/2007 | Lee et al. |
| 7,329,403 B2 | 2/2008 | Chuah et al. |
| 7,347,989 B2 | 3/2008 | Walling |
| 2002/0037264 A1 | 3/2002 | Burry |
| 2002/0068811 A1 | 6/2002 | Ortho |
| 2002/0151453 A1 * | 10/2002 | Abbas et al. .................. 510/447 |
| 2002/0172702 A1 | 11/2002 | Bekele |
| 2003/0185866 A1 | 10/2003 | Franklin |
| 2003/0206973 A1 | 11/2003 | Gale |
| 2004/0001794 A1 | 1/2004 | Withiam et al. |
| 2004/0042985 A1 | 3/2004 | Boncelet |
| 2004/0109833 A1 | 6/2004 | Tang et al. |
| 2004/0198998 A1 | 6/2004 | Tang et al. |
| 2004/0247545 A1 | 12/2004 | Jonas et al. |
| 2005/0100520 A1 | 5/2005 | Hagura et al. |
| 2005/0142085 A1 | 6/2005 | Takeuchi |
| 2005/0163736 A1 * | 7/2005 | Cai et al. ......................... 424/65 |
| 2005/0232881 A1 | 10/2005 | Franklin |
| 2005/0276826 A1 * | 12/2005 | Culver et al. .................. 424/401 |
| 2005/0281851 A1 * | 12/2005 | Cap ................................ 424/401 |
| 2006/0029624 A1 | 2/2006 | Banowski et al. |
| 2006/0029625 A1 * | 2/2006 | Niebauer ....................... 424/401 |
| 2006/0099163 A1 | 5/2006 | Hurley |
| 2006/0115441 A1 | 6/2006 | James et al. |
| 2006/0204463 A1 | 9/2006 | Tang et al. |
| 2007/0196308 A1 | 4/2007 | Popoff et al. |
| 2007/0110687 A1 * | 5/2007 | Mattai ....................... A61K 8/26 424/66 |
| 2007/0166254 A1 | 7/2007 | Bianchi |
| 2007/0178053 A1 | 8/2007 | Franklin |
| 2008/0152608 A1 | 6/2008 | Cropper et al. |
| 2008/0187503 A1 * | 8/2008 | Popoff et al. ................... 424/65 |
| 2008/0187504 A1 | 8/2008 | Fan et al. |
| 2008/0187562 A1 | 8/2008 | Fan |
| 2008/0193393 A1 * | 8/2008 | Dayan ............................. 424/59 |
| 2008/0241089 A1 | 10/2008 | Banowski et al. |
| 2008/0267895 A1 | 10/2008 | Franklin et al. |
| 2009/0010864 A1 | 1/2009 | Banowski et al. |
| 2009/0214457 A1 * | 8/2009 | Dierker .................... A61K 8/02 424/66 |
| 2009/0238786 A1 | 9/2009 | Fishman et al. |
| 2009/0239786 A1 | 9/2009 | Fishman |

FOREIGN PATENT DOCUMENTS

| | | |
|---|---|---|
| EP | 272919 A1 | 6/1988 |
| EP | 2072031 | 6/2009 |
| FR | 2270845 | 12/1975 |
| FR | 2924937 | 6/2009 |
| RU | 2268709 | 1/2006 |
| RU | 2310434 | 11/2007 |
| WO | WO 01/062232 | 8/2001 |
| WO | WO01/622232 | 8/2001 |
| WO | WO 0170185 A2 | 9/2001 |
| WO | WO02/069923 | 9/2002 |
| WO | WO2005/025523 | 3/2005 |
| WO | WO 05/063188 | 7/2005 |
| WO | WO2009/045557 | 4/2009 |
| WO | WO2010/046012 | 4/2010 |

OTHER PUBLICATIONS

International Search Report for PCT/US09/59003 dated Nov. 18, 2010.

Anonymous "Herbal Stick Recipe" (May 1, 2008) XP002603342 Retrived from the internet: URL: http://web.archive.org/web/20080501061956/http://www.electroherbalism.com/Naturopathy/Recipe_and_Formulas/Stick_Deodorant_recipe.htm [retrived on Oct. 4, 2010].

Anonymous "Vegetable fats and oils" Wikipedia XP002603382 Retrived from the internet: URL:http://en.wikipedia.org/wiki/vegetable_fats_oils [retrived on Oct. 5, 2010].

Results of partial International Search Report for PCT/US09/59003 dated Nov. 18, 2010.

Anonymous, 2011, "Caprylic/Capric Triglyceride," Bioexclusive Lexikon, XP5507562, retrieved on Sep. 20, 2011.

Cavanagh et al., 2002, "Biological Activities of Lavender Essential Oil," Phytotherapy Research 16(4):301-308.

Choi, 2005, "Transparent Soap of Two-Tone Color Having Transparent Layer and Opaque Layer, and Its Preparation Method." WPI Database Accession No. 2006-583883 and KR 2005 0093624.

Demand and Response with Article 34 Amendment in International Application No. PCT/US09/058957, dated Jul. 2011.

International Search Report and Written Opinion in International Application No. PCT/US09/058957, dated Feb. 14, 2011.

Osawa et al., 1999, "The Antibacterial Activities of Peppermint Oil and Green Tea Polyphenols, Alone and in Combination, against Enterohemorrhagic *Escherichia coli*," Biocontrol Science 4(1):1-7.

Response to Second Written Opinion with Claim Amendments in International Application No. PCT/US09/058957, dated Dec. 2011.

U.S. Appl. No. 11/671,729.

Written Opinion in International Application No. PCT/US09/058957, dated Nov. 15, 2011.

File History from U.S. Appl. No. 12/671,729 since Jan. 17, 2012.

\* cited by examiner

ANTIPERSPIRANT/DEODORANT COMPOSITION

BACKGROUND OF THE INVENTION

When formulating antiperspirant products, previous expectations were that non-volatile components, such as oils, should be minimized because they would remain on the skin after application and leave an oily feeling. Typically, volatile materials are used as the main carrier for delivery of the antiperspirant and/or deodorant actives to the skin. After application, the volatile materials evaporate. Most commonly, volatile silicone oils, such as cyclomethicone, are used as the main volatile component.

According to U.S. Pat. No. 7,347,989B2 to Walling et al., high levels of non-volatile organic fluids inhibit antiperspirant efficacy by impeding release characteristics from the applied product (see column 1, lines 36-54).

It would be desirable to replace volatile silicone in an antiperspirant/deodorant product because silicone has a limited supply, and as a result, a higher cost. While it would be desirable to make the replacement, the resulting product should have the same product performance and consumer perceptions as products containing volatile silicone.

SUMMARY OF THE INVENTION

A composition comprising a mixing product of at least one material chosen from antiperspirant actives and deodorant actives; greater than 10 weight % of a plant oil; and less than 40 weight % of a volatile silicone oil. In one embodiment, the composition further includes a gellant.

A stick composition comprising a mixing product of greater than 10 weight % of a plant oil; a gellant for the composition: and less than 40 weight % of a volatile silicone oil, wherein the composition does not contain an antiperspirant active or deodorant active.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present invention includes plant (natural) oils in an antiperspirant/deodorant composition that overcomes the expectation that the composition will have an oily feel and leave a white residue.

Plant Oils

The composition includes a plant oil. By plant oil it is meant that the oil is obtained from a plant, or the plant oil can be made by blending of oil components to obtain an oil that is substantially similar in composition to a plant oil. By substantially similar, it is meant that the manufactured oil contains at least 50 weight % (or at least 60, 70, 80, 90, 95, 98, or 99 weight %) of the components that are found in the plant oil that it is designed to mimic.

In certain embodiments, the plant oil has a melting point below 40° C. or below 35° C. or below 30° C.

Examples of the plant oil include, but are not limited to, palm kernel, coconut, avocado, canola, corn, cottonseed, olive, palm, hi-oleic sunflower, mid-oleic sunflower, sunflower, palm stearin, palm kernel olein, safflower, and babassu oils. In one embodiment, palm kernel oil is the selected oil. In another embodiment, coconut oil is the selected oil. In another embodiment, the plant oil is a combination of palm kernel oil and coconut oil.

In certain embodiments, the plant oil is selected to be those that contain at least 40 weight % C12-C14 fatty acids. These oils will provide stick products with greater strength at the same level of oil. In other embodiments, the oil is selected as those oils with lower amounts of unsaturation. Higher levels of unsaturation could result in undesired fragrance when the unsaturated bonds become saturated over time. In certain embodiments, the amount of unsaturated components in the oil is no more than 20, 19, 18, 17, 16, 15, 14, 13, 12, 11, or 10 weight % of the oil.

The tables below show representative compositions of selected oils.

| Chain Length | Name | Palm Kernel | Coconut | Avocado | Babassu | Canola | Corn |
|---|---|---|---|---|---|---|---|
| C6:0 | caproic | <0.8 | <0.6 | 0 | | 0 | 0 |
| C8:0 | caprylic | 2.4-6.2 | 4.6-10 | 0 | | 0 | 0 |
| C10:0 | capric | 2.6-5 | 5.5-8 | 0 | | 0 | 0 |
| C12:0 | lauric | 45-55 | 45.1-50.3 | 0 | 50 | 0 | 0 |
| C14:0 | myristic | 14-18 | 16.8-21 | 0 | 20 | 0 | 0 |
| C16:0 | palmitic | 6.5-10 | 7.5-10.2 | 5-15 | 11 | 4-5 | 11 |
| C16:1 | palmitoleic | 0 | 0 | 5 | | 0 | 0 |
| C18:0 | stearic | 1-3 | 2-4 | 3 | 3.5 | 1.5-2.5 | 2 |
| C18:1 | oleic | 12-19 | 5-10 | 59-74 | 10 | 53-6 | 28 |
| C18:2 | linoleic | 1-3.5 | 1-2.5 | 10-20 | | 20-23 | 58 |
| C18:3 | alpha linoleic | 0 | 0 | 3 | | 9-12 | 1 |
| C20:0 | arachidic | 0 | 0 | 0 | | 0 | 0 |
| C22:0 | behenic | 0 | 0 | 0 | | 0 | 0 |
| C22:1 | erucic | 0 | 0 | 0 | | <2 | 0 |
| Monounsaturates (C18:1) | | 12 | 6 | 71 | | 62 | 28 |
| Polyunsaturates (C18:2 and C18:3) | | 2 | 2 | 14 | | 32 | 59 |
| Saturates (C10:0. C12:0. C14:0. C16:0. C18:0) | | 86 | 92 | 12 | | 6 | 13 |

-continued

| Chain Length | Name | Palm Kernel | Coconut | Avocado | Babassu | Canola | Corn |
|---|---|---|---|---|---|---|---|
| Iodine value (cg/g) | | 14-21 | 6.3-10.6 | 75-95 | | 110-120 | 120-130 |
| Melting Point (° C.) | | 25-30 | 20-28 | <0 | | <0 | <0 |

| Chain Length | Name | Cottonseed | Olive | Palm | Sunflower Hi-oleic | Sunflower Mid-oleic | Sunflower Regular |
|---|---|---|---|---|---|---|---|
| C6:0 | caproic | 0 | 0 | 0 | 0 | No data | 0 |
| C8:0 | caprylic | 0 | 0 | 0 | 0 | No data | 0 |
| C10:0 | capric | 0 | 0 | 0 | 0 | No data | 0 |
| C12:0 | lauric | 0 | 0 | <0.5 | 0 | No data | 0 |
| C14:0 | myristic | 0.6-1 | 0 | 0.5-2 | 0 | No data | 0 |
| C16:0 | palmitic | 21.4-26.4 | 7.5-20 | 39.3-47.5 | 4 | No data | 5-7.6 |
| C16:1 | palmitoleic | 0-1.2 | 0 | 0 | 0 | No data | 0 |
| C18:0 | stearic | 2.1-3.3 | 0.5-5 | 3.5-6 | 6 | No data | 2.7-6.5 |
| C18:1 | oleic | 14.7-21.7 | 55-83 | 36-44 | 85 | 55-65 | 14-39.4 |
| C18:2 | linoleic | 46.7-58.2 | 3.5-21 | 9-12 | 5 | No data | 48.3-74 |
| C18:3 | alpha linoleic | 0-0.4 | <1.5 | <0.3 | 0 | 1 | 0-0.3 |
| C20:0 | arachidic | 0.2-0.5 | <0.8 | 0 | 0 | No data | 0.1-0.5 |
| C22:0 | behenic | 0-0.6 | 0 | 0 | 0 | | 0.3-1.5 |
| C22:1 | erucic | 0 | 0 | 0 | 0 | No data | 0 |
| Monounsaturates (C18:1) | | 19 | 77 | 39 | 85 | 58 | 20 |
| Polyunsaturates (C18:2 and C18:3) | | 55 | 9 | 10 | 5 | 31 | 69 |
| Saturates (C10:0, C12:0, C14:0, C16:0, C18:0) | | 26 | 14 | 51 | 10 | 9 | 11 |
| Iodine value (cg/g) | | 100-115 | 75-94 | 50-55 | 88 | 100-112 | 118-141 |
| Melting Point (° C.) | | <0 | <0 | 37.3 | <0 | <0 | <0 |

The amount of plant oil in the composition is greater than 10 weight % of the composition. In certain embodiments, the amount is greater than 11, 12, 13, 14, 15, 16, 17, 18, 19, 20, 21, 22, 23, 24, or 25 weight % in the composition. In certain embodiments, the amount of plant oil in the composition can be up to about 50 weight % of the composition. In other embodiments, the amount is up to 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, or 11 weight % of the composition. To make a range of amounts, any of the preceding minimum amounts can be paired with any of the preceding maximum amounts. In certain embodiments, the amount of plant oil is greater than the amount of volatile silicone in the composition. In other embodiments, the amount of plant oil is more than 10, 15, 20, 25, 30, 35, 40, 45, 50, 55, 60, 65, 70, 75, 80, 85, 90, or 95 weight % of the combined weight of plant oil and volatile silicone (if present).

Gellants

Gellants are those materials known in the art that structure the composition. Examples include, but are not limited to waxes, fatty alcohol, hydrogenated vegetable oil, a hydrocarbon wax, esters of fatty acid and fatty alcohol, triglycerides, or other cosmetically acceptable materials, which are solid or semi solid at room temperature and provide a consistency suitable for application to the skin.

In one embodiment, the hydrogenated oil is hydrogenated soybean oil. In one embodiment, the hydrogenated soybean oil is almost, but not fully hydrogenated. The amount of hydrogenation is measured by the iodine value. The iodine value can be measured by ASTM D5554-95 (2006). In one embodiment, the iodine value of the hydrogenated soybean oil used herein is greater than 0 to 20. In one embodiment, the iodine value is 1 to 5. In another embodiment, the soybean oil is fully hydrogenated with an iodine value of 0. In another embodiment, the iodine value is up to 20. Reference is made to United States Patent Publication No. 2008/0187504A1.

In one embodiment, the gellant includes a partially hydrogenated soybean oil having an iodine value in the range of about 75 to about 80. This partially hydrogenated soybean oil can be obtained from Cargill under the product designation S-500. Reference is made to United States Patent Publication No. 2008/0187503A1. This material has a typical fatty acid distribution shown in the table below. Amounts shown are in % by weight.

| | |
|---|---|
| C16:0 | 10.5-11.2 |
| C18:0 | 6.8-7.5 |
| C18:1 | 61-65 |
| C18:2 | 16-19 |
| C18:3 | 0-0.2 |
| Saturates | 17.5-19.5 |
| Trans | 34-39 |

The hydrocarbon wax can be a hydrocarbon of the formula $C_nH_{2n+2}$, wherein n is 20-100, and the hydrocarbon is at least 90% linear. In one embodiment, the hydrocarbon is a paraffin. In another embodiment, the hydrocarbon is polyethylene. An example of a polyethylene can be found in U.S. Pat. No. 6,503,491. In another embodiment, the polyethylene has a weight average molecular weight in of about 300 to about 3000 and a melting point of about 50 to about 129° C. In one embodiment, the hydrocarbon is synthetically made from methylene to form a polymethylene.

The fatty alcohol can be any fatty alcohol. In one embodiment, the fatty alcohol is stearyl alcohol.

In another embodiment, the gellant includes hydrogenated castor oil (castor wax). In certain embodiments, the melting point of the castor wax is 70 to 90, or it can be 70, 80, or 90.

In one embodiment, the gellant is a combination of the hydrogenated soybean oil with a fatty alcohol or the hydrocarbon. Reference is made to United States Patent Publication No. 2008/0187504A1.

Fatty Acids

In certain embodiments, the composition includes a fatty acid. The fatty acid is present in its acid form. While fatty acids are present in plant oils, this is an additional amount of fatty acid that is added. In one embodiment, the fatty acid is a saturated fatty acid. In one embodiment, the fatty acid can be selected from any C16 to C18 fatty acid. In one embodiment, the fatty acid can be stearic acid and/or palmitic acid. The amount of fatty acid in the composition is greater than 0 to 7 weight % of the composition. In other embodiments, the amount of fatty acid is at least 0.5, 1, 2, 3, 4, 5, or 6 up to 7 weight %.

Antiperspirant Active Materials

When the composition includes an antiperspirant active, any of the known antiperspirant active materials can be utilized in the composition. Antiperspirant actives include, but are not limited to aluminum chlorhydrate, aluminum chloride, aluminum sesquichlorohydrate, aluminum-zirconium hydroxychlorides, complexes or adducts of the above-mentioned active ingredients with glycol, such as propylene glycol (for example, "Rehydrol" 11 from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category 1 active antiperspirant ingredients, listed in the Food and Drug Administration's Monograph on Antiperspirant Drug Products for overall-the-counter human use (Oct. 10, 1973) can be used.

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al., which is incorporated herein by reference only for the disclosure of the antiperspirant actives.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al., which are incorporated herein by reference only for their disclosure of the antiperspirant active.

In other embodiments, the type of salt of interest, an aluminum zirconium tetrasalt or octasalt free of glycine are used wherein aluminum zirconium salt is stabilized by Betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the Betaine:zirconium mole ratio can be about 0.2:1 to about 3.0:1 (or in other embodiments of about 0.4:1 to about 1.5:1). Another salt that can be used is an aluminum chloride salt buffered by Betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the Betaine:Zr mole ratio is about 0, 2:1 to about 3.0:1 (or in other embodiments of about 0.4:1 to about 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to form a Betaine stabilized active.

Examples of commercially available glycine-free low M:Cl ratio tetrasalts and octasalts include, but are not limited to, REZAL™ AZP 955 CPG and REZAL™ AZP 885 respectively (both from Reheis Chemical Company, Berkeley Heights, N.J.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active. Examples of calcium salt stabilized antiperspirant actives can be found in U.S. Patent Application Publication No. 2006/0204463, which is incorporated herein by reference only for the disclosure of the calcium salt stabilized antiperspirant actives.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

Deodorant Active Materials

Any known deodorant active can be used. Examples of deodorant active include, but are not limited to, antimicrobial actives, alcohols, 2,4,4'-trichloro-2'-hydroxy diphenyl ether (Triclosan), benzethonium chloride, polyhexamethylene biguanides, triethyl citrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats.

Volatile Silicone

Compositions according to the present invention can include a volatile silicone. In some embodiments, volatile silicone is excluded from the composition. In one embodiment, the volatile silicone is a volatile cyclic polydimethylsiloxane (cyclomethicone), e.g., cyclopentasiloxane. By volatile material it is meant that the material has a measurable vapor pressure at ambient temperature. Preferably, the volatile cyclic polydimethylsiloxane is cyclomethicone. Various types of cyclomethicones may be used. Illustratively, and not by way of limitation, the volatile silicones are one or more members selected from cyclic polydimethylsiloxanes such as those represented by Formula 1:

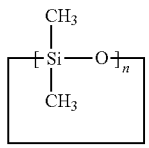

where n is an integer with a value of 3-7, particularly 5-6. Illustrative examples of suitable cyclomethicones are DC-345 and DC-245, manufactured by Dow Corning Corporation, Midland, Mich. These types include a tetramer (octylmethylcyclotetrasiloxane) and a pentamer (decamethylcyclopentasiloxane). In one embodiment, the amount of volatile silicone in the composition is greater than 0 up to 40 weight % of the composition. In another embodiment, the amount is less than 40, 35, 30, 25, 20, 15, 10, 5, or 1 weight % of the composition. In one embodiment, there is no volatile silicone in the composition. In another embodiment, there is no silicone in the composition. In another embodiment, the combined amount of the plant oil and volatile silicone is up to 50, 45, 40, 35, 30, 25, or 20 weight %.

Talc

In certain embodiments, the composition can contain talc. In one embodiment, the amount of talc in the composition is 1 to 10 weight % of the composition.

Emollients

The composition can contain emollients in any desired amount to achieve a desired emollient effect. Emollients are known in the art and are used to impart a soothing effect on the skin. Non-volatile emollients are preferable in the present invention. Classes or non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material in the present invention is phenyl trimethicone. Non limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, cetyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl linolate, paraffin waxes, glycyrrhizic acid, hydrocyethyl stearate amide.

The composition can additionally include ionizable inorganic salts. These ionizable salts are of the form $M_aX_b$ where a=1, or 2 and b=1 or 2; M is a member chosen from $Na^{+1}$, $Li^{+1}$, $K^{+1}$. $Mg^{+2}$, $Ca^{+2}$, $Sr^{+2}$, $Zn^{+2}$ and X is a member chosen chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, and hydrogensulfate. In certain embodiments, the selected salts are chosen from NaCl and $ZnCl_2$. As will be appreciated by those skilled in the art, while it may be possible under certain circumstances to add a salt directly to a portion of the mixture during manufacturing, it is desired to add the salt as a mixture or solution of the salt in a carrier or solvent, particularly water. Of course various concentrations of the salt premix can be made.

The composition may also contain particulates which include but are not limited to talc, mica, fragrance encapsulates, or hydrophobically modified starches, such as aluminum starch octenyl succinate (MACKADERM™ ASTRO-DRY™ from McIntyre Group Ltd.). If the composition is in a liquid form and dispensed through a roll-on applicator, the average particle size of the suspended material is sized so that it can pass through the application to prevent the ball applicator from malfunctioning. Usually, the average particle size does not exceed 150 microns.

In certain embodiments, the composition may also contain as an optional ingredient at least one malodor counteracting alpha, beta-unsaturated ester or mixtures of such materials. In certain embodiments, the level of malodor counteracting composition to deliver a perceivable odor control benefit when delivered from an antiperspirant and/or deodorant composition is about 0.05 to about 0.45 weight % based on the entire composition. The alpha, beta-unsaturated ester malodor counteracting materials are incorporated within the oil phase of an antiperspirant composition. Examples of these malodor counteracting components can be found in U.S. Pat. Nos. 6,610,648 and 6,495,097, which are incorporated herein only for their disclosure of the alpha, beta unsaturated esters. For example, in this invention the odor neutralizing alpha, beta unsaturated ester mixture demonstrates unexpected stability in antiperspirant compositions containing low metal:chloride (M:Cl) ratio salts of free glycine.

Examples of the alpha, beta unsaturated ester include, but are not limited to:

(1) 3-phenyl-2-propenoic acid alkyl esters wherein $R^1$ is a substituent on the benzene ring and is chosen from an alkyl, an alkoxy, an aryl, or a substituted aryl. In certain embodiments, $R^1$ is chosen from H, a $C_1$ to $C_8$ alkyl, a $C_1$ to $C_8$ alkoxy, or an aryl: and $R^2$ is a subsistent group replacing the carboxylic acid hydrogen to form the ester where $R^2$ has greater than 6 carbon atoms, an aryl, or a substituted aryl group, in certain embodiments $R^2$ is a $C_6$ to $C_{12}$ alkyl or is a benzyl group: and (2) an ester of fumaric or maleic acid having linear ester carbon chains from 3-9 carbons, for example dihexyl fumarate;

(3) e-phenyl propenoic acid ester chosen from octyl methoxy cinnamate, phenylethyl cinnamate, benzyl cinnamate:

(4) an aliphatic unsaturated ester, such as dihexyl fumarate.

The composition may optionally further comprise absorbent materials such as corn starch, talc, clay, sodium polyacrylate and/or cotton fiber; and/or other materials such as fragrances, bacteriostats and/or bacteriosides, colorants, etc. Known bacteriostats include baceteriostatic quaternary ammonium compounds such as 2-amino-2-methyl-1-propanol (AMP), cetyl-trimethylammomium bromide, cetyl pyridinium chloride, 2,4,4N-trichloro-2N-hydroxydiphenylether (Triclosan), etc. and various zinc salts.

Antioxidants may be added to the composition, preferably to act as ingredient protectants and for maintenance of long-term stability of the composition. Suitable antioxidants include Tinogard, manufactured by Ciba Specialty Chemicals, Basel, Switzerland.

The compositions as provided herein are described and claimed with reference to their ingredients, as is usual in the art. As would be evident to one skilled in the art, ingredients may in some instances react with one another, so that the true composition of the final formulation may not correspond exactly to the ingredients listed. Thus, it should be understood that the invention extends to the product of the combination of the listed ingredients.

The compositions of the present invention may be manufactured using methods known in the art. Typically, the ingredients are combined and heated to melt the components (other than inert filler), and the melted components (together with particulate inert filler) are mixed. Desirably, volatile materials, such as the fragrance materials, are incorporated in the composition in the latter stages of the mixing cycle, in order to avoid volatilization thereof. After mixing, the molten composition can be poured directly into the dispensers, after which the compositions harden into a solid, and the container is capped to preserve the product until use.

In one embodiment, the composition is a solid stick or soft solid when at ambient room temperature of about 25° C. The stick form is an example of a solid form, and the soft solid is a thickened form that may or may not be solid. The stick form can be distinguished from a soft solid in that, in a stick, the formulated product can retain its shape for extended time periods outside the package, the product not loosing its shape significantly (allowing for some shrinkage due to solvent evaporation). Adjustment of amounts of gelling or thickening agents can be used in order to form a soft solid or stick.

Soft solids can be suitably packaged in containers that have the appearance of a stick, but which dispense through apertures (for example, slots or pores) on the top surface of the package. The soft solid products have also been called soft sticks or "smooth-ons", and hereinafter are generically called "soft solids". Reference is made to U.S. Pat. Nos. 5,102,656, 5,069,897, and 4,937,069.

In one embodiment, the composition is an anhydrous stick. By anhydrous it is meant that no separate water is added but there could be moisture associated with materials that are added to the composition. In certain embodiments, the amount of water is zero or less than 3, 2, 1, 0.5, or 0.1 weight % of the composition.

In one embodiment, the compression force of the composition is at least 2500 g. In other embodiments, the compression force is at least 3000 g. at least 3500 g, at least 4000 g, at least 4500 g, at least about 5000 g. at least 6000 g, at least 7000 g. at least about 8000 g, at least 9000 g. In another embodiment, the compression force is 2500 g to 10.000 g.

In one embodiment, the composition can provide a payout of about 0.7 to about 0.9 g according to the payout test on the Payout, Glide, and Flakeoff Test Machine, which is the machine and method described in US 2010/0269564, the United States counterpart to (WO2009/0455571). In another embodiment, the composition can provide a glide of about 0.8 to about 1.4 g according to the glide test on the Payout, Glide, and Flakeoff Test Machine. In another embodiment, the composition can provide a flakeoff of less that about 25%. In other embodiments, the flake off is less than about 20, about 15, about 10, or about 5%. In other embodiments, the amount of flakeoff is about 1 to about 6%.

Compression strength of a stick product is measured using a Texture Analyzer Model # TA-ZT21 from Texture Technologies. The compression probe is a 19 mm square end probe. The antiperspirant stick is removed from the barrel and placed in a hardness sample holder. The stick is positioned such that 2.54 cm (1 inch) of the sample, measured at the edge of the domed portion, is exposed for the test. The cover on the hardness holder is closed and the holder positioned so that the blade comes in contact with the midpoint of the exposed sample. The instrument is set to the following parameters:
Measured Force—compression (speed set at 1.0 mm/s)
Option—RETURN TO START
Distance—5.0 mm
Unit selection—grams.
The measurements to be recorded are peak force and distance required to break the stick.
The higher the force reading, the stronger the stick. The longer the distance to break, the more elastic the stick.
For rheology of a soft solid sample, the following procedure is used for the AR-1000 Instrument:
(i) Instrument preparation.
  Turn on the computer, turn on air, remove cap from rheometer, screw on geometry, turn on instrument, turn on water circulator. Open the rheology software—AR Instrument Control. Under the geometry tab, select the geometry to be used for testing (Soft solid-20 mm parallel plate). Next, the gap between the geometry and the pettier plate is zeroed from the instrument menu at the top by choosing gap and then zero gap. Follow the instructions on screen to zero the gap. This is a calibration step to accurately measure the distance between the geometry and the plate. Once the gap has been zeroed, set up the procedure. Under the procedure menu, select new flow, a flow tab will appear in the main screen. Under the flow tab, select conditioning step in the left screen. Set the temperature to 37° C. Next, in the flow step window, set up a stepped flow procedure with the following parameters: Temperature (37° C.); Ramp: Shear Stress (Pa); Range (0.1-6000 Pa); Mode (linear); Number of points (600).

(ii) Sample Preparation.

Place sample in stainless steel cutting jig. Advance the product until curved portion of the product has cleared the jig's edge. Use the wire slicer to remove the curved portion of the product, and discard. The cross-section of the product should now be at its maximum width. Advance the product so that 3-4 mm of product is exposed past the edge of the jig. Again, use the wire to cut off the exposed product, creating a 3-4 mm thick slab of product. Cut the slab in half widthwise so there is no hole in the sample from the screw. This is the sample to be tested. Gently place the 3-4 mm thick slab of product directly onto the pettier plate, being careful to minimize the amount of shear applied to the sample. The sample should be as close to the epicenter of the plate as possible. Set the instrument gap to 1100 micron. While the geometry is being lowered, gently reposition the sample so that it is directly under the geometry. This is to ensure that when the geometry and sample come in contact with one another, the sample takes up the entire surface area of the geometry. When the geometry has stopped at the 1100 micron gap, use a spatula to trim excess product from the edge of the geometry. Lower the geometry to 1000 micron. Begin the test by clicking the run experiment button.

(iii) Data Analysis

The instrument applies increasing stress to the geometry, scanning the preset range 0.1-6000 Pa. The software then plots the log viscosity (y variable) of the sample as a function of the shear stress (x variable). To better quantify the rheological characteristics of a sample, look at 3 numbers: static yield stress, dynamic yield stress, and delta stress. Static yield stress is the stress at which the instrument can first accurately measure the sample's viscosity, i.e. the first data point on the graph. Dynamic stress is the stress at which the sample's viscosity starts to rapidly decrease. This portion of the curve will have an almost vertical slope. The final number, delta stress is the difference between static yield stress and dynamic yield stress.

In another embodiment, the composition is a stick that does not contain an antiperspirant or deodorant active. In this embodiment, the stick can be formulated to be a lip balm, lipstick, or a cosmetic.

SPECIFIC EMBODIMENTS OF THE INVENTION

The invention is further described in the following examples. The examples are merely illustrative and do not in any way limit the scope of the invention as described and claimed. The stick compositions are made using the procedures described above. The amounts in the formulas below are weight %.

The following are a comparative control and two formulations according to the invention. Formula 1 is an example of a stick composition with about 53.4 weight % of the silicone replaced with palm kernel oil based on the combined amount of silicone and palm kernel oil. Formula 2 is an example of a stick composition without any silicone.

| Material | Control | Formula 1 | Formula 2 |
| --- | --- | --- | --- |
| C12-15 Alkyl Benzoate | 10 | 0 | 16.9 |
| PPG-14 Butyl Ether | 6 | 16.65 | 0 |
| Hydrogenated soybean oil Iodine value greater than 0 to about 20 | 2 | 2 | 2 |
| Hydrogenated Castor Oil (Melting Point 80° C.) | 5 | 5 | 5 |
| PEG-8 Distearate | 3 | 3 | 3 |
| Stearyl Alcohol | 16 | 16 | 16 |
| Behenyl Alcohol | 0.15 | 0.15 | 0.15 |
| Palm Kernel Oil | 0 | 18.7 | 35 |
| Aluminum Zirconium Tetrachlorohydrex Gly | 20 | 20 | 20 |
| Cyclomethicone | 33.9 | 16.5 | 0 |
| Talc | 2 | 0 | 0 |
| Fragrance and Minors | QS to 100 | QS to 100 | QS to 100 |

The example below is a demonstration that the plant oil containing composition can provide the same level of sweat reduction efficacy as a product without the plant oil. In this example, formulas 1 and 2 were compared to the control formula to determine the level of sweat reduction efficacy. A 3 cell hot room clinical test was conducted. All products were applied at an equivalent dose of 0.5 grams/axilla/application. Eighty-one (81) male volunteers with shaved underarms participated in the study.

Method

Recruit male panelists, age 18 to 55.

Refrain from A/P and talcum powder use for 21 days prior to beginning the study, Two days before the study, the panelists underarms were shaved by professional barbers (shave foam/razor).

Begin study with one group on Monday and a second group on Tuesday.

On day 1, obtain baseline sweat collections following standard hot room procedures for round robin designs, wash axillae, first application using a randomization for 4-celled test.

On day 2, wash axillae, second application,

On day 3, wash axillae, third application,

On day 4, wash axillae, fourth application,

On day 5. 24-hour sweat collection post #4.

Data analysis was performed at using SAS statistics software. The data from both groups of panelists were combined for analysis. The results are shown in the table below.

|                              | Control | Formula 2 | Formula 1 |
|------------------------------|---------|-----------|-----------|
| Baseline output (g)          | 1088    | 1185      | 1176      |
| Post-treatment output (g)    | 1071    | 1003      | 1070      |
| Estimated % sweat reduction  | 7.7     | 15.0      | 11.2      |

Corrected Mean Difference

|                                  |                                       |                                       |
|----------------------------------|---------------------------------------|---------------------------------------|
|                                  | 5.7% fav Formula 2                    | 3.6% fav Formula 2                    |
| 95% C.I. for Mean Difference     | (-1.1, 12.9)                          | (-3.1, 10.7)                          |
| p-value                          | 0.0996                                | 0.2938                                |

Corrected Mean Difference

|                              |                   |
|------------------------------|-------------------|
|                              | 2.0% fav Formula 1|
| 95% C.I. for Mean Difference | (-4.5, 9.0)       |
| p-value                      | 0.5481            |

Mean Square Error: 0.0223

The clinical efficacy results showed: overall, Control, Formula 1, and Formula 2 performed at statistical parity to each other, p>0.05, and Formula 1 performed at statistical parity to Formula 2, p=0.2938.

In contrast to what was expected, the compositions with natural oils had parity performance to a product containing silicone without natural oil.

Below are additional formulas that can be made according to the invention.

| Material | Formula 3 | Formula 4 | Formula 5 | Formula 6 |
|---|---|---|---|---|
| C12-15 Alkyl Benzoate | 16.65 | 8.6 | 12.2 | 10.1 |
| PPG-14 Butyl Ether | 0 | 8.6 | 4.2 | 6.1 |
| Hydrogenated soybean oil Iodine value greater than 0 to about 20 | 2 | 2 | 2 | 2 |
| Hydrogenated Castor Oil (Melting Point 80° C.) | 5 | 5 | 5 | 5 |
| PEG-8 Distearate | 3 | 3 | 3 | 3 |
| Stearyl Alcohol | 16 | 16 | 16 | 16.1 |
| Behenyl Alcohol | 0.15 | 0.15 | 0.15 | 0.15 |
| Palm Kernel Oil | 26.7 | 34.7 | 30.3 | 15.8 |
| Aluminum Zirconium Tetrachlorohydrex Gly | 20 | 20 | 20 | 20.2 |
| Cyclomethicone | 8.5 | 0 | 4.1 | 18.4 |
| Talc | 0 | 0 | 1 | 1 |
| Fragrance and Minors | QS to 100 | QS to 100 | QS to 100 | QS to 100 |

Ten female judges evaluate the sensory properties of the control formula and formulas 1-5, with each panelist assessing each product twice using an assessment scale (15-pt scale). Samples are blinded and coded with a random three-digit number. The order of sample presentation is balanced and randomized across panelists. Each panelist tests 2 products per session, one on each arm. Each panelist pre-washes her underarm with soap, and then pats dry. They stay in an environmental room for 10 minutes. 5 minutes with arms down and 5 minutes with arms up to allow air flow under the arm before they apply a specified amount (4 strokes) of each sample on her underarm. The panelist evaluate each test product on application, visual, and tactile attributes at several time points (e.g. 15 minutes after application) including Glideability, Evenness of Spread, Coolness, Hardness, Whiteness, Stickiness, Wetness, Amount of Residue, Waxy Residue, Powderiness, Oily/Greasy Residue. After underarm evaluation, each panelist wipes her underarm with baby wipes before reapplying product to underarm following the application procedure. A swatch, 15.2 cm×17.8 cm (6"×7") black cotton fabric, is applied on the underarm. Arm is held against torso for 10 seconds, fabric is removed and evaluated for rub-off white residue and other residue.

The table below shows how each formula comparatively performed against the control formula.

|  | Formula | | | | |
|---|---|---|---|---|---|
|  | 3 | 1 | 2 | 4 | 5 |
| Glide-1 Stroke | < | < | < | < | < |
| Glide-4 Stroke | < | < | < | < | < |
| Stick Hardness | > | > | > | > | > |
| Smooth-Application | < | < | < | < | < |
| Wet-Application | = | < | = | = | < |
| Sticky-Application | = | > | = | = | = |
| Slip-Application | < | < | < | < | < |
| Slip-2 Minutes | = | = | < | = | = |
| Slip-5 Minutes | = | = | < | = | = |
| Slip-15 Minutes | > | = | = | > | = |
| Whiteness-Application | < | = | < | = | = |
| Amt Res-Application | < | < | = | = | < |
| Amt Res-2 Minutes | = | < | = | = | < |
| Amt Res-5 Minutes | = | < | = | = | < |
| Amt Res-10 Minutes | = | < | < | = | < |
| Amt Res-20 Minutes | > | = | > | > | > |
| Oily/Grease Res-Application | < | < | = | = | < |
| Oily/Grease Res-2 Minutes | = | < | = | = | < |
| Oily/Grease Res-5 Minutes | = | < | = | = | < |
| Oily/Grease Res-10 Minutes | = | < | < | = | < |
| Oily/Grease Res-20 Minutes | > | = | > | > | > |
| Oily/Grease Res-25 Minutes | > | = | > | > | = |
| Oily/Grease Res-30 Minutes | = | = | > | = | = |
| Powder-25 Minutes | < | < | < | < | < |
| Powder-30 Minutes | < | < | < | < | < |
| Black Cloth: | | | | | |
| Rub-off-White Residue | < | = | < | < | < |
| Other Residue-Cloth | < | = | < | = | = |
| Payout (g/underarm) | = | = | = | > | = |

<: Product had a significantly lower value for that attribute vs. control
>: Product had a significantly higher value for that attribute vs. control
=: parity performance vs. control Below are examples of formulations using other plant oils.

| Material | A | B | C | D |
|---|---|---|---|---|
| C12-15 Alkyl Benzoate | 10.1 | 10.1 | 10.1 | 10.1 |
| PPG-14 Butyl Ether | 6 | 6 | 6 | 6 |
| Hydrogenated soybean oil Iodine value greater than 0 to about 20 | 2 | 2 | 2 | 2 |
| Hydrogenated Castor Oil (Melting Point 80° C.) | 5 | 5 | 5 | 5 |
| PEG-8 Distearate | 3 | 3 | 3 | 3 |
| Stearyl Alcohol | 16.1 | 16.1 | 16.1 | 16.1 |
| Behenyl Alcohol | 0.15 | 0.15 | 0.15 | 0.15 |
| Coconut Oil | 15.8 | 0 | 0 | 0 |
| Hi oleic sunflower oil | 0 | 15.8 | 0 | 0 |
| Sunflower Oil | 0 | 0 | 15.8 | 0 |
| Olive Oil (extra virgin) | 0 | 0 | 0 | 15.8 |
| Aluminum Zirconium Tetrachlorohydrex Gly | 20.2 | 20.2 | 20.1 | 20.2 |
| Cyclomethicone | 18.4 | 18.4 | 18.4 | 18.4 |
| Talc | 2 | 2 | 2 | |
| Fragrance and Minors | QS to 100 | QS to 100 | QS to 100 | QS to 100 |

What is claimed is:

1. A composition, comprising a mixing product of:
   at least one material chosen from antiperspirant actives and deodorant actives;
   greater than 10% weight % of plant oil;
   4.1-18.4 weight % of a volatile silicone oil;
   0-16.9 weight % of $C_{12-15}$ alkyl benzoate; and
   0-16.65 weight % of polypropylene glycol (PPG)-14 butyl ether;
   wherein the composition comprises no talc.

2. The composition of claim 1, further comprising one or more emollients that are not alkyl benzoate and PPG-14 butyl ether.

3. The composition of claim 1, wherein the volatile silicone oil is cyclomethicone.

4. The composition of claim 1, wherein the at least one deodorant active comprises a compound selected from benzethonium chloride, polyhexamethylene biguanides, and triethyl citrate.

5. The composition of claim 1, wherein the composition comprises
   18.7 weight % of plant oil;
   16.5 weight % of a volatile silicone oil;
   16.65 weight % of PPG-14 butyl ether; and
   0 weight % of C12-15 $C_{12-15}$ alkyl benzoate.

6. The composition of claim 1, wherein the composition comprises
   35 weight % of plant oil;
   0 weight % of PPG-14 butyl ether; and
   16.9 weight % of $C_{12-15}$ alkyl benzoate.

7. The composition of claim 1, wherein the plant oil is palm kernel oil.

8. The composition of claim 1, wherein the plant oil comprises at least 86 weight % of saturated $C_{10}$-$C_{18}$ fatty acids.

9. The composition of claim 1, wherein the composition is an anhydrous stick product.

10. The composition of claim 1, further comprising a gellant that comprises a partially hydrogenated soybean oil having an iodine value greater than or equal to about 75 and less than or equal to about 80.

11. The composition of claim 1, further comprising a gellant that comprises a partially hydrogenated soybean oil comprising greater than or equal to 17.5 weight % of saturated $C_{10}$-$C_{18}$ fatty acids and less than or equal to 19.5 weight % of saturated $C_{10}$-$C_{18}$ fatty acids.

12. The composition of claim 1 as a stick product that has a payout greater than or equal to about 0.7 grams and less than or equal to about 0.9 grams according to a payout test on a payout-glide-flakeoff apparatus.

13. The composition of claim 1 as a stick product that has a glide greater than or equal to about 0.8 grams and less than or equal to about 1.4 grams according to a glide test on a payout-glide-flakeoff apparatus.

14. The composition of claim 1, which is a stick product that has a flakeoff greater than or equal to about 1% and less than or equal to about 6% on a payout-glide-flakeoff apparatus.

15. The composition of claim 1, wherein the composition comprises
   18.7 weight % of palm kernel oil;
   16.5 weight % of a volatile silicone oil;
   16.65 weight % of PPG-14 butyl ether; and
   0 weight % of $C_{12-15}$ alkyl benzoate.

16. The composition of claim 1, wherein the composition comprises
   35 weight % of palm kernel oil;
   0 weight % of PPG-14 butyl ether; and
   16.9 weight % of $C_{12-15}$ alkyl benzoate.

* * * * *

UNITED STATES PATENT AND TRADEMARK OFFICE
CERTIFICATE OF CORRECTION

PATENT NO. : 11,058,904 B2
APPLICATION NO. : 12/671715
DATED : July 13, 2021
INVENTOR(S) : H. Steven Misner et al.

Page 1 of 1

It is certified that error appears in the above-identified patent and that said Letters Patent is hereby corrected as shown below:

On the Title Page

On Page 2, item (56) under "OTHER PUBLICATIONS" Line 29, delete "." and insert -- filed February 6, 2007. --, therefor.

In the Specification

In Column 8, Line 29, delete "linolate," and insert -- lanolate, --, therefor.

In the Claims

In Column 15, Line 27, in Claim 1, delete "10%", and insert -- 10 --, therefor.

In Column 15, Line 47, in Claim 5, delete "C12-15".

Signed and Sealed this
Fifth Day of October, 2021

Drew Hirshfeld
*Performing the Functions and Duties of the
Under Secretary of Commerce for Intellectual Property and
Director of the United States Patent and Trademark Office*